(12) United States Patent
Devos et al.

(10) Patent No.: US 11,744,863 B2
(45) Date of Patent: Sep. 5, 2023

(54) PROCESS FOR PREPARING A POOLED HUMAN PLATELET LYSATE, POOLED HUMAN PLATELET LYSATE AND ITS USE FOR TREATING NEUROLOGICAL DISORDERS

(71) Applicants: CENTRE HOSPITALIER REGIONAL ET UNIVERSITAIRE DE LILLE (CHRU), Lille (FR); UNIVERSITE DE LILLE, Lille (FR); UNIVERSITE DU LITTORAL COTE D'OPALE, Dunkirk (FR); INSERM (INSTITUT NATIONAL DE LA SANTE ET DE LA RECHERCHE MEDICALE), Paris (FR); TAIPEI MEDICAL UNIVERSITY, Taipei (TW)

(72) Inventors: David Devos, Marcq-en-Baroeul (FR); Thierry Burnouf, Lille (FR); Jean-christophe Devedjian, Lille (FR); Ming-Li Chou, Taoyuan (TW); Flore Gouel, Ostricourt (FR)

(73) Assignees: Centre Hospitalier Regional et Universitaire De Lille (CHRU), Lille (FR); UNIVERSITE DE LILLE 2 DROIT ET SANTE, Lille (FR); UNIVERSITE DU LITTORAL COTE D'OPALE, Dunkirk (FR); INSTITUT NATIONAL DE LA SANTE ET DE LA RECHERCHE MEDICALE (INSERM), Paris (FR); TAIPEI MEDICAL UNIVERSITY, Taipei (TW)

(*) Notice: Subject to any disclaimer, the term of this patent is extended or adjusted under 35 U.S.C. 154(b) by 656 days.

(21) Appl. No.: 16/622,446

(22) PCT Filed: Jun. 15, 2018

(86) PCT No.: PCT/EP2018/066020
§ 371 (c)(1),
(2) Date: Dec. 13, 2019

(87) PCT Pub. No.: WO2018/229278
PCT Pub. Date: Dec. 20, 2018

(65) Prior Publication Data
US 2020/0113942 A1 Apr. 16, 2020

(30) Foreign Application Priority Data
Jun. 16, 2017 (EP) .................... 17305739

(51) Int. Cl.
A61K 35/19 (2015.01)
A61P 25/28 (2006.01)
A61K 9/00 (2006.01)
C12N 5/078 (2010.01)

(52) U.S. Cl.
CPC ............ A61K 35/19 (2013.01); A61K 9/0085 (2013.01); A61P 25/28 (2018.01); C12N 5/0644 (2013.01)

(58) Field of Classification Search
CPC ....... A61K 35/19; A61K 9/0085; A61P 25/28; C12N 5/0644
See application file for complete search history.

(56) References Cited

U.S. PATENT DOCUMENTS

2012/0156306 A1 6/2012 Weissman et al.
2013/0143810 A1 6/2013 Burnouf et al.
2014/0179602 A1 6/2014 Weissman et al.
2016/0074481 A1 3/2016 Burnouf et al.

FOREIGN PATENT DOCUMENTS

WO 2013003356 A1 1/2013

OTHER PUBLICATIONS

Burnouf et al., Biotechnol. Appl. Biochem., 2010, 56, p. 151-160. (Year: 2010).*
Ferdinand et al., Exp. & Trans. Stroke Med., 2016, 8(9), 8 pages. (Year: 2016).*
Anitua et al., PLoS One 2013, 8(9): e73118, 13 pages. (Year: 2013).*
The International Search Report and Written Opinion, dated Sep. 12, 2018, in the corresponding PCT Appl. No. PCT/EP2018/066020.
Copland Ian B et al: "The effect of platelet lysate fibrinogen on the functionality of MSCs in immunotherapy", Biomaterials, vol. 34, No. 32, Jul. 24, 2013 (Jul. 24, 2013), pp. 7840-7850, XP028686800.
Hayon Yael et al: "Platelet lysates stimulate angiogenesis, neurogenesis and neuroprotection after stroke.", Thrombosis and Haemostasis Aug. 2013, vol. 110, No. 2, Aug. 2013 (Aug. 2013), pp. 323-330, XP002775847.
Flore Gouel et al: "The protective effect of human platelet lysate in models of neurodegenerative disease: involvement of the Akt and MEK pathways : Protective effect of platelet lysate in models of neurodegenerative disease", Journal of Tissue Engineering and Regenerative Medicine, Jan. 1, 2016 (Jan. 1, 2016), XP055427285.
Huang EJ, Reichardt LF., "Neurotrophins: roles in neuronal development and function," Annu Rev Neurosci 2001;24: 677-736.

(Continued)

Primary Examiner — Jonathan S Lau

(57) ABSTRACT

Process for preparing a heat-treated pooled human platelet lysate, said process comprising the steps of: a) Providing a pooled human platelet lysate (p HPL), b) Heat-treating the pooled human platelet lysate at a temperature of 50° C. to 70° C. during 20 to 40 minutes, c) Purifying the heat-treated pooled human platelet lysate of step b).

13 Claims, 6 Drawing Sheets

(56) References Cited

OTHER PUBLICATIONS

Figure 1:
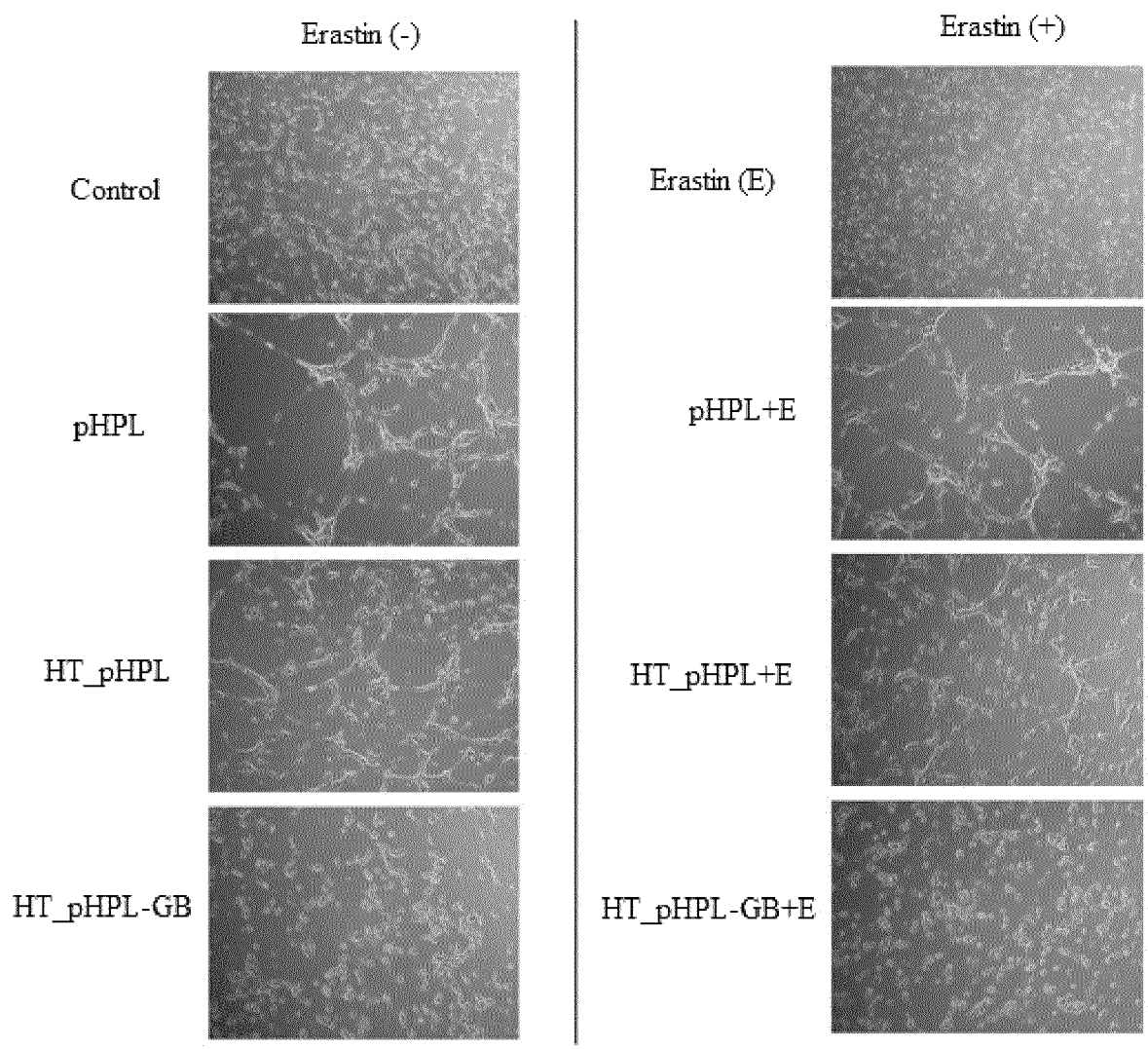

Mohapel P, Frielingsdorf H, Haggblad J, et al. "Platelet-derived growth factor (PDGF-BB) and brain-derived neurotrophic factor (BDNF) induce striatal neurogenesis in adult rats with 6-hydroxydopamine lesions," Neuroscience 2005;132: 767-76.
Gonzalez-Aparicio R, Flores JA, Fernandez-Espejo E., "Antiparkinsonian trophic action of glial cell line-derived neurotrophic factor and transforming growth factor beta 1 is enhanced after co-infusion in rats," Experimental Neurology 2010;226: 136-47.
Kirik D, Georgievska B, Bjorklund A., "Localized striatal delivery of GDNF as a treatment for Parkinson disease," Nat Neurosci 2004;7: 105-10.
Golebiewska EM, Poole AW, "Platelet secretion: From haemostasis to wound healing and beyond," Blood Rev. May 2015;29(3):153-62.
Burnouf T, Goubran HA, Chen TM, et al., "Blood-derived biomaterials and, platelet growth factors in regenerative medicine," Blood Rev 2013;27: 77-89.
Burnouf T, Strunk D, Koh M, et al., "Human platelet lysate: replacing fetal bovine serum as a gold standard for human cell propagation?" Biomaterials 2016;76: 371-87.
Scholz D, Poltl D, Genewsky A, et al., "Rapid, complete and large-scale generation of post-mitotic neurons from the human LUHMES cell line," J Neurochem 2011;119: 957-71.
J.K. Ryu, D.Davalos and K.Akassoglou., "Fibrinogen signal transduction in the nervous system. Journal of thrombosis and heamostasis," 2009; vol. 7, issue supplement s1, 151-154.
Tsu-Bi Shih D, Burnouf T., "Preparation, quality criteria, and properties of human blood platelet lysate supplements for ex vivo stem cell expansion," New Biotechnology 2015; vol. 32, No. 1.
Victor E. Santo, Manuela E.Gomes, Joao F. Mano and Rui L; Reis, "Chitosan-chondrotin sulphate nanoparticles for controlled delivery of platelet lysates in bone regenerative medicine," Journal of Tissue Engineering and Regenerative Medicine. Dec. 2012, vol. 6, issue S3, pp. s47-s59.
Ming-Li Chou, "Dedicated, virally-inactivated, platelet lysates and platelet microparticles in regenerative medicine and neuroprotective therapies," Human health and pathology. Universite du Droit et de la Sante—Lille II; Taipei medical university (Taipei), 2016, https://tel.archives-ouvertes.fr/tel-01973786.
Choi et al., "Effect of platelet lysate on growth and sulfated glycosaminoglycan synthesis in articular chondrocyte cultures," Arthritis & Rheumatism, USA, 1980, vol. 23, NR:2, pp. 220-224.
Gouel et al., "The protective effect of human platelet lysate in models of neurodegenerative disease: involvement of the Akt and MEK pathways," Journal of Tissue Engineering and Regenerative Medicine, USA, Dec. 12, 2016, vol. 11, pp. 3236-3240. (Abstract).
The English translation of the Japanese Office Action, dated Jun. 20, 2022, in the related Japanese Appl. No. 2019-569741.
The search report, dated Feb. 24, 2022, in the related Russian Appl. No. 2020101295/04(001897).
Chou et al., "Tailor-made purified human platelet lysate concentrated in neurotrophins for treatment of Parkinson's disease," Biomaterials, vol. 142, pp. 77-89, Oct. 2017.
The English translation of the Russian Office Action, dated Jul. 28, 2022, in the related Russian Application No. 2020101295.
Frolova et al., "Neuroprotectors in pediatric practice," Oct. 25, 2016. (Machine-generated English translation included.).

* cited by examiner

PROCESS FOR PREPARING A POOLED HUMAN PLATELET LYSATE, POOLED HUMAN PLATELET LYSATE AND ITS USE FOR TREATING NEUROLOGICAL DISORDERS

This application is a National Stage Application of PCT/EP2018/066020 filed Jun. 15, 2018, which claims priority from European Patent Application No. 17305739.9 filed Jun. 16, 2017. Each of the prior mentioned applications is hereby incorporated by reference herein in its entirety.

The present invention relates to a process for obtaining a novel pooled human platelet lysate, the pooled human platelet lysate itself and its use for treating neurological disorders such as neurodegenerative, neuroinflammatory, neurodevelopmental and/or neurovascular disorders (i.e. stroke), but also the consequences of cerebral insults (traumatic brain injury, hypoxia . . . ).

Developing effective "disease modifying strategy" providing neuroprotection, neurorestoration and neurogenesis to treat neurodegenerative disorders, such as Parkinson's disease (PD), amyotrophic lateral sclerosis (ALS), and Alzheimer disease (AD), is urgently needed considering the huge societal and economic impacts these disorders impose to patients and care-givers.

Developing effective treatments providing neurorestoration and neurogenesis in order to compensate for the loss of neurons and following insults of the central nervous system, such as severe hypoxia following delivery or cardiac arrest or severe traumatic brain injury, is also largely waited considering the lack of validated treatments.

There is substantial evidence that neurotrophins, as activators and modulators of neuronal signaling pathways, represent a logical therapeutic strategy for neurological disorders[1]. Application of single recombinant neurotrophic growth factors has provided encouraging results for neuronal protection and repair in both cell and animal models.

Platelet-derived growth factor-CC (PDGF-CC) proved to be a potent neuroprotective factor in several animal models of neuronal injury whereas PDGF-BB and brain-derived neurotrophic factor (BDNF), administered via intra cerebroventricular (ICV) route, stimulated neurogenesis[2]. In addition, systemic administration of BDNF in a photothrombotic model of focal stroke could induce neurogenesis and improve sensorimotor function. Transforming growth factor-β (TGF-β) could promote the development and survival of dopaminergic neurons, and neuroprotection in animal models of parkinsonism, and enhanced the trophic effect of glial-derived neurotrophic factor (GDNF) in hemiparkinsonian rats[3].

Pre-clinical studies showed neuroprotection by basic-fibroblast growth factor (b-FGF) and vascular endothelial growth factor-β (VEGF-β), and promotion of neuroprotection and neurorestoration by GDNF[4].

Unfortunately, all randomized clinical studies involving ICV administration of high-dose, single growth factors have failed to yield any substantial positive clinical effects.

Currently, administering single neurotrophins in such complex and multifaceted neurodegenerative pathologies is insufficient to yield meaningful therapeutic outcomes.

Thus, there is a need to develop a novel approach combining several recombinant neurotrophins, which would likely be more powerful, but this is conceptually challenging in particular to seek regulatory approval, thereby justifying more pragmatic strategies inspired from other fields of regenerative medicine.

Platelet concentrates are a well-established therapeutic product, on the WHO model list of essential medicines, typically used in the prophylaxis and treatment of bleeding disorders resulting from thrombocytopenia. Besides their role in haemostasis, platelets exert crucial physiological functions in wound healing and tissue repair[5].

The range of regenerative medicine[6] and cell therapy[7] applications where platelets and platelet lysates are evaluated is expanding. The therapeutic benefit of platelets in tissue healing is multifactorial and results from the myriad of bioactive mediators stored primarily in the α-granules and acting in synergy. These include neurotrophic growth factors, such as PDGF (-AA, -AB and -BB isoforms), BDNF, VEGF, TGF-β, bFGF, or epithelium growth factor (EGF). Intracranial delivery of platelet lysates in animal models of stroke was recently shown to stimulate the proliferation of endogenous neural stem cells (eNSC) and angiogenesis in the subventricular zone and in the peri-lesion cortex, leading to improved functional outcomes and reduced injury, and suggesting neuroprotective effects[8].

Document US 2014/0176602 proposes a viral inactivated biological mixture and its preparation. Particularly, this document describes a method for preparing a viral-safe platelet extract, the method comprising the following steps of providing a platelet-enriched fraction from more than one donor, carrying out a solvent detergent (S/D) viral inactivation treatment, contacting the S/D treated material with a non-toxic amphiphilic polymer, removing the S/D and subjecting the material to at least one more orthogonal viral inactivation treatment. The orthogonal viral inactivation may be a pasteurization which is carried out at 60° C. for 10 hours in presence of stabilizers such as sucrose and glycine.

Document US 2012/0156306 describes a viral-safe platelet extract, said extract being non-clottable. Particularly, this document describes a method for preparing a viral-safe platelet extract said method comprising at least two orthogonal viral inactivation treatments e.g. solvent detergent (S/D) viral inactivation treatment and heat inactivation. The heat inactivation is a pasteurization which is carried out at 60° C. for 10 hours in order to destroy both lipid-enveloped and non-enveloped viruses. Sucrose and glycine were added to the solution to serve as stabilizers during the pasteurization.

In the two documents cited above, the resulting viral-safe platelet extracts exhibit high fibrinogen content thanks to the presence of stabilizers during the pasteurization step. Indeed, it is known from document U.S. Pat. No. 5,116,950 that the stabilizers, such as sucrose or glycine, exert an effect of highly stabilizing fibrinogen upon liquid heating. Table 1 particularly shows that the addition of sucrose provides particularly excellent stabilizing effect.

Document US 2016/0074481 relates to the field of platelet derivatives and more specifically to the field of growth factors concentrates which are obtained from platelets. Particularly, it is disclosed a method for preparing a clottable concentrate of platelet growth factors. By the term "clottable", it is meant that the concentrate of platelet growth factors comprises both fibrinogen and coagulation factor XIII. Specifically, the concentration of fibrinogen in the clottable concentrate of platelet growth factors is preferably higher than 1, more preferably higher than 1.5, and even more preferably higher than 2.5 g/L of the concentrate.

Document US 2013/0143810 concerns human platelet extracts rich in growth factors for wound healing and stem cell expansion. This document relates to a virally-inactivated growth factors-containing platelet lysate depleted of PDGF and VEGF, which is preferably enriched in TGF, IGF and EGF-rich. It is described in table 1 that compositions of S/D treated platelet concentrate after oil extraction (S/D-PC-O) and after charcoal treatment (S/D-PC-OC) exhibit a fibrinogen concentration of 4.5±0.3 mg/mL and 2.65±0.7 mg/mL respectively.

B. Copland et al. ("*The effect of platelet lysate fibrinogen on the functionality of MSCs in immunotherapy*" Biomaterials 34 (2013) 7840-7850) investigated platelet lysate depleted of fibrinogen as a product for expanding human MSCs for use in immunomodulation therapy. FIG. 2c is a comparison of fibrinogen content from preparations of fibrinogen depleted platelet lysate. Each batch described by B. Copland exhibits a fibrinogen content of at least 4 mg/mL.

Document WO 2013/003356 describes compositions comprising platelet lysates depleted of fibrinogen, said compositions being used as cell culture medium. The depletion of fibrinogen from platelet lysate is performed using heparin and metal salts. Moreover, said compositions depleted in fibrinogen have a concentration of fibrinogen of about 2 or 4 µg/mL.

However, platelet lysates contain plasma-borne fibrinogen, a protein that plays a causative role in neurologic disorders as a potent inducer of inflammation and an inhibitor of neurite outgrowth[9]. This may be a reason why application of platelet lysates in the field of neurodegenerative disorders in humans, such as Parkinson's Disease, has not been reported yet.

The invention is based on the unexpected findings that, when pooled human platelet lysate (pHPL) is treated under specific conditions, it is able to potentiate the treatment of neurological disorders by inducing better neuroprotective effect as well as neurorestoration.

A pooled human platelet lysate according to the invention is a human platelet lysate obtained from at least two platelet lysates from different donors. Preferably, the pooled human platelet lysate is obtained from at least 5, at least 10, at least 20, at least 30, at least 40, at least 50, at least 100, at least 140, at least 180 at least 200 and more particularly, from at least 240 different platelet lysates collected from different donors.

Particularly, the inventors have discovered that heat-treatment of pHPL reduces the total protein content of the lysate and promotes enhanced neuroprotective and neurorestoration potential.

Thus, in a first aspect, the present invention relates to a process for preparing a heat-treated pooled human platelet lysate, said process comprising the steps of:
  a) Providing a pooled human platelet lysate (pHPL),
  b) Heat-treating the pooled human platelet lysate at a temperature of 55° C. to 65° C. during 20 to 40 minutes,
  c) Purifying the heat-treated pooled human platelet lysate of step b).

The process of the invention leads to a heat-treated pooled human platelet lysate (HT_pHPL) having a fibrinogen content of less than 5%, less than 4%, less than 3%, less than 2, less than 1% and more preferably less than 0.1% by weight of the fibrinogen content of non-heat-treated pHPL. The fibrinogen concentration of the heat-treated pHPL is less than 50 ng/mL, less than 40 ng/mL, less than 30 ng/mL, less than 20 ng/mL, and more preferably less than 15 ng/mL.

Particularly, the heat-treated pHPL is free of fibrinogen. By the expression "free of fibrinogen" it is meant that the fibrinogen concentration in the HT_pHPL does not exceed 15 ng/mL, particularly does not exceed 10 ng/mL and more particularly, does not exceed 5 ng/mL.

According to the invention, the first step of the process consists in providing a pooled human platelet lysate (pHPL). This pHPL may be prepared according to well-known methods from platelet concentrate (PC), which induce the release of growth factors and other active molecules.

For example, the pHPL may be prepared by the method comprising the following steps of:
  i) providing platelet concentrates,
  ii) lysing separately each platelet concentrate of step i), and
  iii) mixing the lysates resulting from step ii) in order to obtain a pooled human platelet lysate.

The platelet concentrates provided in step i) may come from different donors and may be obtained by suitable standard collection methods from allogeneic platelet sources. Particularly, the platelet concentrate may be obtained from whole blood using the buffy coat or platelet-rich plasma (PRP) technique, or may be collected by apheresis technique. Preferably, the platelet concentrate is produced from whole blood using the buffy coat or (PRP) technique[10].

In the "PRP method", anticoagulated whole blood is centrifuged using a soft spin under conditions validated to segregate red blood cells (RBC) from the upper half containing a platelet and plasma mixture, so called PRP. Platelets are then concentrated by hard spin centrifugation with validated acceleration and deceleration curves. The platelet concentrate bag is left stationary at room temperature and then the concentrate is resuspended in plasma. In the "buffy coat" method, anticoagulated whole blood is centrifuged using a hard spin with validated acceleration and deceleration curves to separate 'cell-free" plasma on the top layer, a middle layer called buffy coat (BC) and a red blood cells (RBC) bottom layer. The BC layer is transferred to a satellite bag. A small quantity of plasma is returned to the BC layer and gently mixed before again being subjected to light spinning centrifugation with validated acceleration and deceleration curves. The PRP supernatant is then placed in platelet storage and may be store at 22+/−2° C.

In the apheresis method, the platelet concentrates may be obtained through an extracorporeal medical device used in blood donation that separates the platelets and returns other portions of the blood to the donor.

The plasma used for suspending the concentrate in the "PRP method", the plasma returned to BC layer in the "buffy coat" method, or the plasma collected with platelet by apheresis may be substituted by a platelet additive solution (PAS) or by a mixture between plasma and PAS, and preferably by a mixture between plasma and PAS. Said mixture between plasma and PAS may contain from about 30% to 40% by weight of plasma and from about 70% to 60% by weight of PAS.

The platelet concentrate provided in step i) may be subjected to a leucodepletion treatment. This treatment leads to leucocyte depletion and it may be achieved by filtration on a leucoreduction filter or during the platelet collection by apheresis.

The platelet concentrate provided in step i) may be subjected to a step of viral/pathogen inactivation treatment before lysis. The viral/pathogen inactivation treatment applied to the platelet concentrate may be selected from Intercept® Blood system (from Cerus Corporation), Mirasol® PRT system (from Terumo BCT), or THERAFLEX-UV (from Macopharma). These procedures are well-known by one skilled in the art and target, with or without the addition of a photo-inactivating agent, the alteration of nucleic acids.

In one embodiment, the platelet concentrate is subjected to a leucodepletion treatment and to a viral/pathogen inactivation treatment. Preferably, the leucodepletion treatment is performed before the viral/pathogen inactivation treatment.

The step ii) of lysing separately each platelet concentrates may be achieved by any method known in the art. For example, platelet lysis may be achieved by one or more freeze/thaw cycles, by platelet activation induced by addition of thrombin or $CaCl_2$, by sonication or by solvent/detergent (S/D) treatment. Preferably, step ii) of lysing the platelet concentrates is achieved by one or more freeze/thaw cycles, and more preferably by at least three cycles. When lysis is achieved by one of the preceding method, a centrifugation and filtration step may also be performed to remove cell debris.

Then, step iii) consists in mixing the lysates in order to obtain a pool of HPL, also called pHPL. Thus, the pool of HPL is obtained by mixing the lysed platelet concentrates from at least 2 platelet lysates from different donors. Preferably, the pool of HPL is obtained by mixing at least 5, at least 10, at least 20, at least 30, at least 40, at least 50, at least 100, at least 140, at least 180, at least 200 and more particularly, at least 240 different platelet lysates collected from different donors.

A suitable pooled human platelet lysate (pHPL) for the process of the invention may be any pooled human platelet lysate from blood establishments or from commercial suppliers. For example, the pooled human platelet lysate may be obtained from Macopharma (Tourcoing, France; MultiPL'30® Human platelet lysate), from Cook-Regentec (Indianapolis, USA; Stemulate® Human platelet lysate), from Stemcell Technologies (Grenoble, France; Human platelet Lysate) or also from Sigma-Aldrich (PLTMax® Human Platelet Lysate).

The second step of the process of the invention consists in heat-treating the pHPL. This step is preferably performed without adding the stabilizers that are classically used to maintain the biologic activity of proteins. Such stabilizers are for example sucrose, sorbitol, mannitol or amino acids such as arginine or lysine. Heat-treatment may preferably be performed at a temperature of about 50° C. to 70° C., preferably of about 52° C. to 60° C., and more preferably at a temperature of about 56° C. The most promising results in terms of reproducibility of neuroprotection and neurorestoration were indeed obtained for pHPL treated at about 56° C.

In a preferred embodiment, the duration of the heat-treatment is about 20 to 40 minutes, preferably about 30 minutes.

Moreover, after heat-treatment, the pHPL may be cooled down for at least 5 minutes, preferably to a temperature of about 2 to 5° C., before purifying step c).

Advantageously, the heat-treated pHPL provided in step a) may be subjected before step b) to a treatment which induces an activation of the coagulation cascade. For example, the heat-treated pHPL may be mixed with glass beads (GB) and $CaCl_2$ under stirring, or using $CaCl_2$ alone. This treatment leads to a clot formation that is removed after centrifugation and the resulting pHPL is thus free of fibrinogen. Without wanting to be bound by any theory, the inventors believe that this treatment contributes to lower toxicity and improved neuroprotective effect of the pHPL according to the invention.

The third step of the process of the invention consists in purifying the heat-treated pooled human platelet lysate. This purification step may be carried out by any method known in the art, such as for example centrifugation or filtration.

Centrifugation may advantageously be carried out at a temperature of about 2 to 6° C., for example for at least 10 min at 9000×g to 11000×g.

When filtration is used, the heat-treated pHPL is advantageously passed through a filter having a pore size from 5 µm to 0.2 µm, preferably a sequence of two or more successive filters having decreasing pore sizes with a respective pore size from 5 µm to 0.2 µm is used.

Advantageously, purification of the heat-treated pHPL lysate in step c) is carried out by centrifugation. Without wanting to be bound by any theory, the inventors believe that centrifugation at low temperatures as described above may contribute to further removing cold-insoluble components, such as fibrinogen, which precipitate.

The process of the present invention may further comprise a step of freezing and storing the heat-treated pHPL obtained in step c) at a temperature range from −20° C. to −85° C., preferably from −25° C. to −50° C. and more preferably around −30° C. Alternatively, the heat-treated pHPL may be freeze-dried before storing.

In one embodiment, the process of the present invention further comprises after step b), and before optional freezing or freeze-drying, a step of viral inactivation or virus removal and/or prion removal. Suitable viral inactivation or virus removal methods include but are not limited to solvent/detergent treatment (S/D treatment), detergent treatment only, pasteurization, steam treatment or vapor treatment, UV treatment, gamma irradiation, low pH treatment, caprylic acid treatment and nanofiltration. For example, the S/D treatment may be performed using 1% of Tri-butyl-phosphate and 1% Triton X-100 at 31° C. for 1 hour. The pasteurization treatment may be performed by a heat-treatment at 60° C. for 10 hours in the presence of stabilizers. The nanofiltration may be performed using dedicated virus filters of 15, 20, or 35 nm, or equivalent pathogen removal filters known in the art.

Thus, in this embodiment, the obtained heat-treated pHPL is virally-safe. The term "viral inactivation" refers to a situation wherein viruses are maintained in the human platelet lysate but are rendered non-viable e.g. by dissolving their lipid coat or by destroying their virion structure. The term "virus removal" refers to a situation wherein viruses, which have rigid large size structures, are removed from the human platelet lysate by retention on a nanofilter while human platelet lysate components go through such virus removal filter and is recovered for further processing.

Advantageously, the process according to the invention is suitable with industrial scale production of large quantity of a standardized heat-treated pHPL (HT_pHPL). Indeed, by using a pooled human platelet lysate as starting material, particularly a pHPL from industrial suppliers, the process allows to produce a HT_pHPL which providing high level of standardization and consistency, and also complying with principles of GMPs. The obtained HT_pHPL may thus be standardized which is particularly advantageous when the HT_pHPL is intended to be used in biotherapy, notably through brain administration.

Surprisingly and unexpectedly, the process according to the invention leads to a heat-treated pHPL, which provides improved neuroprotection compared to non heat-treated pHPL. In vitro assays have shown that the pHPL prepared according to the invention protects dopaminergic cells from death induced by neurotoxins and without inducing morphologic alteration. Without wanting to be bound by any theory the inventors believe that improved neuroprotective activity of the HT_pHPL of the invention is a result of its reduced total protein content, such as the fibrinogen content.

Indeed, it is believed that the heat-treatment at a temperature of 50° C. to 70° C. induces precipitation of proteins leading, after step c) in which it is believed that the precipitated proteins are removed, to a total protein content in the HT_pHPL according to the invention significantly lower than in the starting pHPL.

Particularly, it is also believed that the heat-treatment results in significant reduction or depletion of fibrinogen and proteolytic enzymes, such as thrombin, or thrombin-like, or thrombin-generating coagulation factors in the pHPL, and that the heat-treatment step precipitates and/or inactivates potentially toxic heat-unstable proteins and favorably modifies the protein and growth factor balance in the pHPL. Thus, the heat-treated pHPL, contrary to the pHPL, may avoid the biological risk of fibrin formation, which is toxic for the brain. Therefore, the obtained heat-treated pHPL according to the invention offers a substantially higher safety margin than standard human platelet lysates suspended in plasma. Thus, the heat-treated pHPL of the invention is more suitable and more efficient for use in biotherapy, especially through brain administration.

As set forth above, heat-treated pooled human platelet lysate (HT_pHPL) of the invention provides improved neuroprotective and neurorestoration activity.

In a second aspect, the invention relates to a heat-treated pooled human platelet lysate (HT_pHPL) having a fibrinogen content of less than 5%, less than 4%, less than 3%, less than 2, less than 1% and more preferably less than 0.1% by weight of the fibrinogen content of non-heat-treated pHPL. The fibrinogen concentration of the heat-treated pHPL is less than 50 ng/mL, less than 40 ng/mL, less than 30 ng/mL, less than 20 ng/mL, and more preferably less than 15 ng/mL. As shown in the examples section, the heat-treated pooled human platelet lysate according to the invention is neuroprotective.

Particularly, the heat-treated pHPL is free of fibrinogen. By the expression "free of fibrinogen" it is meant that the fibrinogen concentration in the HT_pHPL does not exceed 15 ng/mL, particularly does not exceed 10 ng/mL and more particularly, does not exceed 5 ng/mL. The heat-treated pHPL according to the invention may be obtained by the process described hereabove.

In a third aspect, the invention relates to the heat-treated pooled human platelet lysate according to the invention for use as a biological drug or "biotherapy".

Indeed, thanks to its improved neuroprotective activity and its higher safety, the pooled human platelet lysate may be used in the treatment and/or prevention of a neurological disorder and preferably a neurodegenerative disorder. Thus, the heat-treated pooled human platelet lysates display a strong neuroprotective activity and are particularly advantageous for treating disorder wherein a loss of neuron is observed.

In other terms, the invention also relates to a method of treating and/or preventing neurological disorders, comprising the administration of a therapeutically effective amount of the heat-treated pHPL of the invention, to a patient in need thereof. Preferably the patient is a warm-blooded animal, more preferably a human.

Neurological disorders within the meaning of present invention include but are not limited to neurodegenerative disorders, neurovascular disorders, neuroinflammatory disorders, neurodevelopmental disorders such as autism, cerebral insult such as severe hypoxia following delivery or cardiac arrest or severe cranial traumatism/traumatic brain injury that is to say severe insults resulting in a significant loss of neurons leading to handicap.

Neurodegenerative disorders within the meaning of the present invention include, but are not limited to multiple sclerosis (MS), Parkinson's disease (PD), Huntington's disease (HD), Amyotrophic lateral sclerosis (ALS), stroke, age-related macular degeneration (AMD), degenerative diseases of the retina, and dementia, the latter including, without being limited thereto, Alzheimer's disease (AD), vascular dementia, frontotemporal dementia, semantic dementia and dementia with Lewy bodies. Preferred neurodegenerative diseases are multiple sclerosis, Alzheimer's disease, Parkinson's disease, Huntington's disease, amyotrophic lateral sclerosis.

In a preferred embodiment, the neurodegenerative disorder is selected from Parkinson's disease, amyotrophic lateral sclerosis and Alzheimer's disease. In a particularly preferred embodiment, the neurodegenerative disorder is Parkinson's disease. In another preferred embodiment, the neurodegenerative disorder is amyotrophic lateral sclerosis.

Preferred other neurological disorders include insults of the central nervous system such as severe hypoxia following delivery or cardiac arrest or severe cranial traumatism that is to say severe insults resulting in a significant loss of neurons leading to handicap. The early treatment, with the heat-treated pHPL, following the insult could enhance the physiological neurorestoration and neurogenesis abilities.

The heat-treated pHPL may be administered as such, be encapsulated in natural or synthetic nanoparticles[11] or microparticles or be comprised in a pharmaceutical solution further comprising at least one pharmaceutically acceptable carrier, diluent, excipient and/or adjuvant. The pharmaceutical solution can further comprise complexes, molecules, peptides, salts, vectors or any other compound, which can ameliorate or can be beneficial in treatment neurological disorders.

The route of administration, and the dosage regimen naturally depend upon the severity of the illness, the age, weight, and sex of the patient, etc.

The heat-treated pHPL of the invention may be used for the treatment of any patient, especially a warm-blooded animal such as a mammal and preferably a human.

Advantageously, the heat-treated pHPL according to the invention is suitable for brain administration. Specifically, said heat-treated pHPL is adapted for intra thecal (e.g. for amyotrophic lateral sclerosis which is a pathology of the spinal cord) or intra cerebroventricular (ICV) administration, for example into the right lateral ventricle, preferably closed to the intraventricular foramen so that the heat-treated pHPL can be administrated into the third ventricle. Brain administration may be achieved by the methods known in the art. For example, brain administration may be carried out with a drug delivery system, such as a programmable medication pump.

The administration of the heat-treated pHPL of the invention may also be performed by any other method known by the person skilled in the art, such as for example, intranasal, intramuscular or intraocular administration, or perfusion or infusion of an organ (i.e. direct infusion of a part of the brain tissue).

The exposure dosage used for the administration may be adapted as a function of various parameters, and in particular as a function of the mode of administration used, of the relevant pathology or of the desired duration of treatment.

Definitions

The definitions and explanations below are for the terms as used throughout the entire application, including both the specification and the claims.

By "neuroprotective activity" or "neuroprotection" is meant preservation of neuronal structure and/or function of neuronal cells affected by neurotoxin compared to neuronal cells, which are not affected by neurotoxin. Neuroprotection aims to prevent or slow the disease progression and secondary injuries by halting or at least slowing the loss of neurons. For example, it refers to preservation of the number of neurons in the striatum and/or in the substantia nigra pars compacta of patients affected by Parkinson's disease compared to patients who are not affected by Parkinson's disease.

By "neurorestoration" is meant compensation of existing alterations and stimulation of structural and functional restoring of the injured nervous activity.

The term "patient" refers to a warm-blooded animal, more preferably a human, who/which is awaiting or receiving medical care or is or will be the object of a medical procedure.

The term "human" refers to subjects of both genders and at any stage of development (i.e. neonate, infant, juvenile, adolescent, adult). In one embodiment, the human is an adolescent or adult, preferably an adult.

The terms "treat", "treating" and "treatment", as used herein, are meant to include alleviating or abrogating a condition or disease and/or its attendant symptoms.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "therapeutically effective amount" (or more simply an "effective amount") as used herein means the amount of the heat-treated pHPL of the invention, which is sufficient to achieve the desired therapeutic or prophylactic effect in the individual to which it is administered.

The term "administration", or a variant thereof (e.g., "administering"), means providing the heat-treated pHPL of the invention, alone or as part of a pharmaceutically acceptable solution, to the patient in whom/which the condition, symptom, or disorder is to be treated or prevented.

The present invention will be better understood with reference to the following examples and figures. These examples are intended to representative of specific embodiments of the invention, and are not intended as limiting the scope of the invention.

FIGURES

FIG. 1: Morphologic observation of treated Luhmes cells. Representative pictures of Luhmes cells (×10) after treatment with pHPL, HT_pHPL and HT_pHPL-GB without erastin (left column) or with erastin (right column) exposure.

pHPL: pooled human platelet lysate.

HT_pHPL: heat-treated pooled human platelet lysate.

HT_pHPL-GB: heat-treated pooled human platelet lysate after glass beads and $CaCl_2$ treatment.

Figure 2:
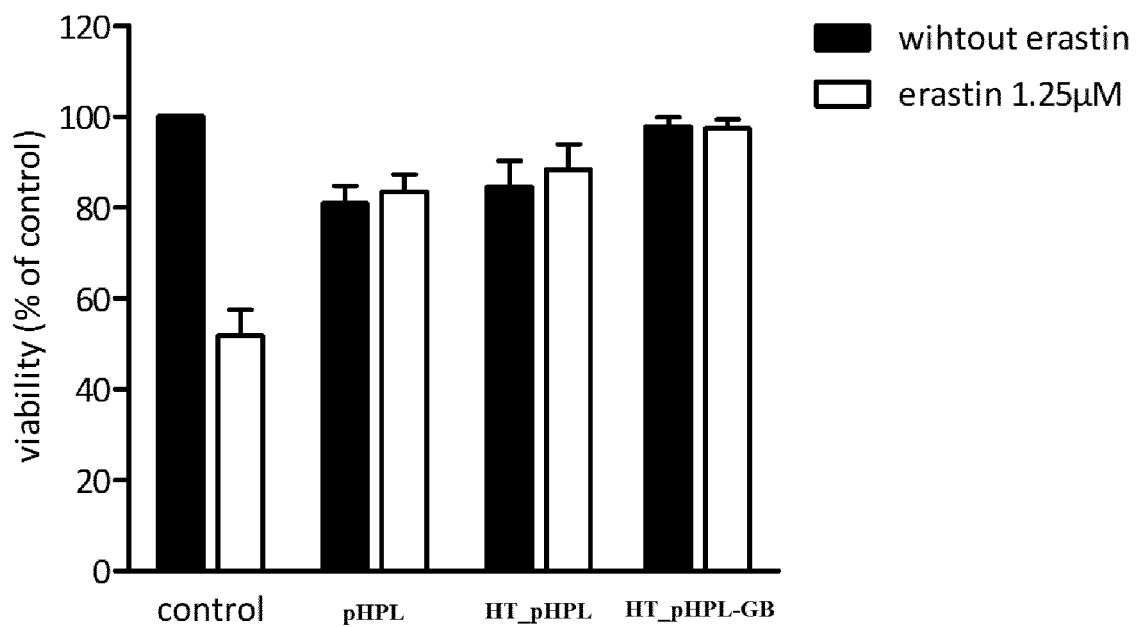

FIG. 2: Flow-cytometry assay. Viability measured by propidium iodide assay and normalized to the control (non treated cells)+/−standard error of the mean (SEM) (n=4).

Figure 3:
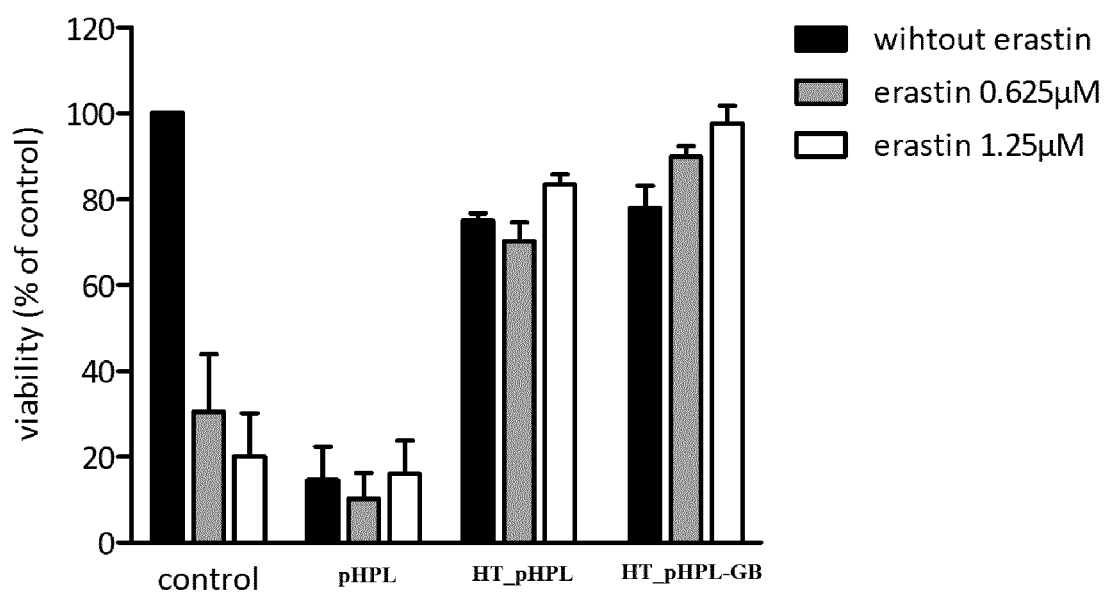

FIG. 3: Resazurin assay. Viability measured by resazurin assay and normalized to the control (non treated cells)+/− SEM (n=3).

Figure 4:
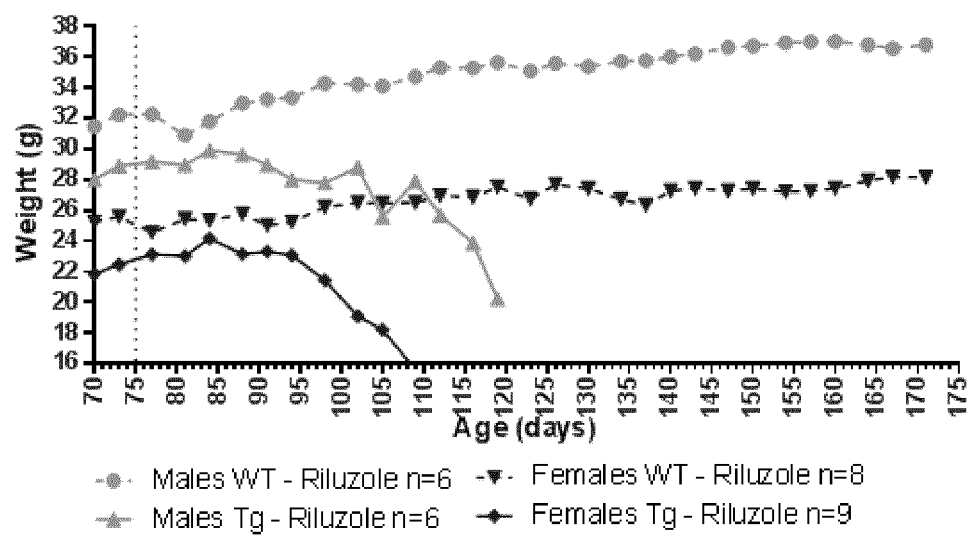

FIG. 4: Body weight evolution of females and males mice treated by Riluzole. Males WT: Males wild-type, Males Tg: males FVB-Tg(Sod1*G86R), Females WT: Females wild-type, Females Tg: females FVB-Tg(Sod1*G86R).

Figure 5:
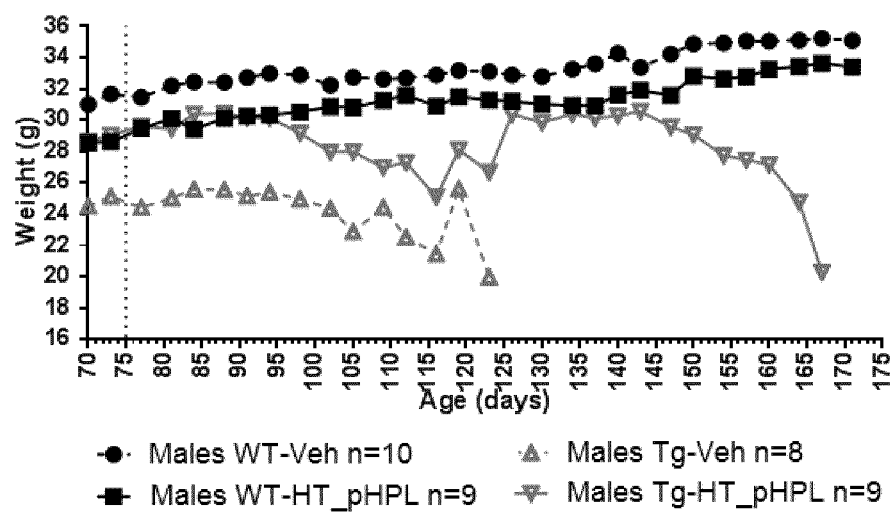

FIG. 5: Body weight evolution of male mice treated by vehicle and HT_pHPL. Veh: Vehicle, Males WT: Males wild-type, Males Tg: males FVB-Tg(Sod1*G86R), HT_pHPL: heat-treated pooled human platelet lysate.

Figure 6:
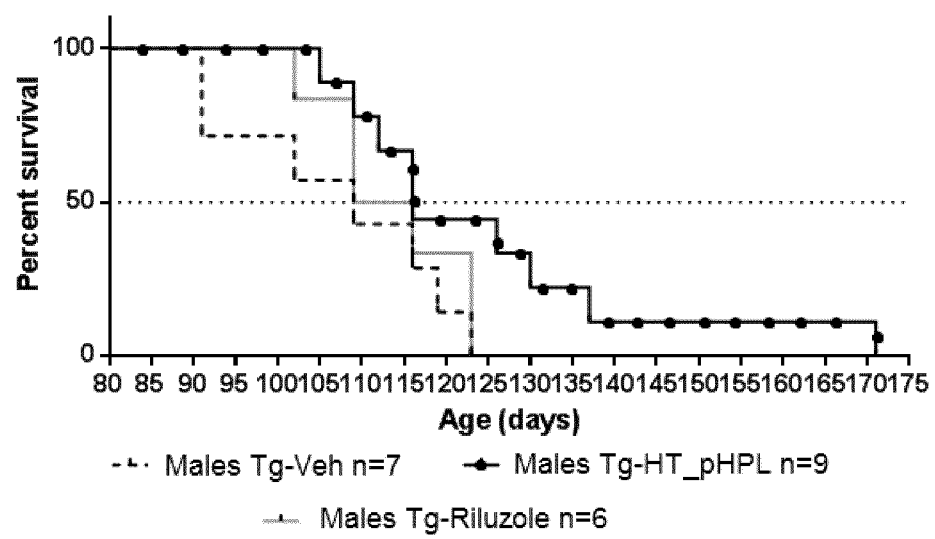

FIG. 6: Survival curve of male mice treated by vehicle, Riluzole and HT_pHPL. Veh: Vehicle, Males Tg: males FVB-Tg(Sod1*G86R), HT_pHPL: heat-treated pooled human platelet lysate.

EXAMPLES

Materials and Methods

1. Preparation of Platelet Lysate pHPL: The pooled human platelet lysate was obtained from Macopharma (Tourcoing, France) under the name MultiPL'30® Human platelet lysate, reference BC0190020.

HT_pHPL: pHPL subjected to heat-treatment at 56° C. for 30 min and purified by centrifugation (15 minutes, 10000 g, 4° C.).

HT_pHPL-GB: pHPL was mixed with 0.5 g/L of glass beads (BEAD-002-1 kg of 2 mm of diameter, from Labbox) and $CaCl_2$ (30 µg/mL and 23 mM final concentration; C4901 Calcium chloride anhydrous powder, from Sigma-Aldrich) under stirring for 1 h.

It was leading within 30 minutes to a clot formation that was removed after centrifugation (6000 g, 30 minutes, 22° C.). The supernatant was heated at 56° C. for 30 minutes and centrifuged before aliquots were made and stored at −80° C. for further use.

2. LUHMES Cells Maintenance and Differentiation

LUHMES cells were obtained from Dr. Scholz's laboratory (University of Konstanz, Germany) and cultured as described[12].

Briefly, undifferentiated LUHMES cells were propagated using Nunclon™ (Nunc, Roskilde, Denmark) plastic cell culture flasks and multi-well plates that were pre-coated with 50 µg/mL poly-L-ornithine and 1 µg/mL fibronectin (Sigma-Aldrich, St. Louis, Mo., USA) in distilled water for 3 h at 37° C. After removal of the coating solution, culture flasks were washed with sterile distilled water and air-dried.

Cells were grown at 37° C. in a humidified 95% air, 5% $CO_2$ atmosphere. The proliferation medium was Advanced Dulbecco's Eagle's medium (Advanced DMEM)/F12 containing 1×N-2 supplement (Invitrogen, Karlsruhe, Germany), 2 mM L-glutamine (Gibco, Rockville, Md., USA) and 40 ng/mL recombinant bFGF (R&D Systems). When reaching approximately 80% confluence, cells were dissociated with a 0.025% trypsin solution (Gibco, Rockville, Md., USA) and passaged at $3 \times 10^6$ cells/flask.

To induce differentiation into neuronal cells, $2 \times 10^6$ LUHMES were seeded and grown into a T75 flask in proliferation medium for 48 h, then in Advanced DMEM/F12 containing 1×N-2 supplement, 2 mM L-glutamine (Gibco), 1 mM dibutyryl cAMP (Sigma-Aldrich), 1 µg/mL tetracycline (Sigma-Aldrich) and 2 ng/mL recombinant human GDNF (R&D Systems). After two days of culture in differentiation condition, LUHMES were cultured to 24-well plate for further experiments at day six.

3. Evaluation of Toxicity and Protective Ability on Dopaminergic Neurons of the Different Platelet Lysates (PL).

The toxicity and the protective ability of the three platelet lysates (pHPL, HT_pHPL, HT_pHPL-GB) were evaluated on the dopaminergic cell line called Luhmes (after 6 days of differentiation).

In the neuroprotective studies, the different PL were assayed against cell death induced by erastin i.e. a very powerful inducer of cell death in dopaminergic neurons).

LUHMES were differentiated for 6 days and the different PL were added (at 5% v/v) into the medium 1 h before treatment with erastin.

In each studies, viability was evaluated by flow-cytometry (propidium iodide) in 24 wells or by resazurin assay in 96 wells-plate at 7 days of differentiation (24 h after PL treatment).

Flow-Cytometry Assay

Experiments are performed to quantify the toxicity and the neuroprotective ability of the different PL by propidium iodide incorporation. LUHMES were cultured in 24 wells-plate.

The flow-cytometer used for the experiments is the CyAn™ model with a 488 nm laser (Beckman Coulter).

Resazurin Assay

To confirm the results obtained by flow-cytometry assay, LUHMES viability was also measured by a colorimetric test, the resazurin assay (performed in 96 wells-plate). This is performed directly on the cell culture, without trypsinization (and the harvesting of the cells), which seemed interesting in light of the experiments done with the flow-cytometer.

4. pH Measurement

To measure the pH in the different platelet lysates, pH test strips from Macherey-Nagel were used (pH Fix 6.0-10.0, reference 921 22).

5. Fibrinogen Dosage

The fibrinogen concentration was measured in different platelet concentrates (pHPL, HT_pHPL and HT_pHPL-GB) by an ELISA (R&D Systems). For each platelet concentrates, measurements were made in duplicate. Concentrations are expressed in ng/mL.

6. Statistical Analysis

Results are expressed as the mean±standard error of the mean (SEM). Statistical analyses were performed using one-way ANOVA after checking for the normal distribution of the data. Non-parametric texts of Wilcoxon and Kruskal-Wallis were performed in case of non-normal distribution. A p value of <0.05 was considered statistically significant.

Results

Morphologic Observation of Treated LUHMES Cells

As shown in FIG. 1, without Erastin exposure the typical shape of the Luhmes cells at 7 days of differentiation was observable in the control. Important changes in the cellular morphology were noted in the presence of pHPL, HT_pHPL, with a propensity to "cluster" the cells. This aspect was not observed when using HT_pHPL-GB.

Under erastin exposure, the typical shape of dying cells is only observed without any treatment by the platelet lysates. This seemed to indicate that HT_pHPL and HT_pHPL-GB were able to afford neuroprotection. Clustered cells still appeared in the presence of pHPL, but were not observed when cells were treated with platelet lysates subjected to GB and heat treatments. Without wanting to be bound by any theory, the inventors believe that it confirms a possible negative role of fibrinogen presence in the pHPL in the formation of these clusters.

Flow-Cytometry Assay

The addition of pHPL induced an apparent gelation of the medium. This was not observed with others lysate preparations. Moreover, analysis by flow-cytometry assay requires obtaining separated cells (by trypsinisation). This step that was very difficult to achieve when the cells were treated with pHPL. Nevertheless viability studies were possible with all the treatments (FIG. 2).

No lysate preparation had a toxic effect. Only pHPL alone slightly decreased the viability (≈85%) compared to the control and the others preparations. But this may be due to the difficulty to separate the cells.

Erastin killed efficiently the control cells, but cell death was not observed when LUHMES cells were treated by HT_pHPL and HT_pHPL-GB. Therefore we concluded that the pooled human platelet lysate according to the invention displays strong protective ability on LUHMES cells.

Resazurin Assay

First of all, cell viability values presented without erastin exposure confirmed that the heat-treated pooled human platelet lysate according to the invention seemed harmless for LUHMES cells.

Results with pHPL were possibly due to an artefact in the experiment. In fact the gelation of the medium (probably due to fibrinogen present in pHPL) seemed to inhibit the mixing of resazurin to the medium, preventing resazurin to penetrate the cells and thus leading to a lack of detection (the loss of viability of approximately 15% did not correspond to the microscopic observation showing that almost all the cells in these wells showed expected morphologies of alive cells).

Erastin killed efficiently the LUHMES cells at the two doses tested and the heat-treated pooled human platelet lysate was able to prevent its toxic effect (Once again the problem of resazurin absorption by the cells due to pHPL treatment is observable).

Fibrinogen Content

The results of fibrinogen concentration for each platelet concentrates are presented in table 1 below:

TABLE 1

|  | Concentration (ng/mL) |
| --- | --- |
| pHPL | 503810 |
| HT_pHPL | 14 |
| HT_pHPL-GB | 11 |

The results exhibit that the heat-treatment step according to the invention leads to a drastic reduction of fibrinogen concentration in the pHPL. Indeed, more than 99.9% of the fibrinogen was removed. At least, the combination of the two treatments is able to reduce the fibrinogen concentration in the pHPL more than the heat-treatment step alone.

Thus, by the heat-treatment step, the obtained heat-treated pooled human platelet lysate, contrary to the pHPL, may be considered as free of fibrinogen. As the heat-treated pooled human platelet lysate is intended to be used for brain administration, this characteristic is particularly advantageous because the cerebrospinal fluid contains less than 1 mg/mL of proteins. Thus, the less is the fibrinogen concentration in the pHPL, the better is the prevention of protein overload.

pH of the Medium

The strips gave the following results:
pH between 7 and 7.3 for pHPL,
pH 7 for HT_pHPL, and
pH 6 for HT_pHPL-GB.

The pH decrease in HT_pHPL-GB could be due to $CaCl_2$ used in the protocol.

However, no modification of pH medium after treatment with the platelet lysates (showed by phenol red indicator) was observed.

Toxicity and Protective Ability on Dopaminergic Neurons

These results show, first, that the heat-treated pooled human platelet lysates (HT_pHPL and HT_pHPL-GB) do not induce toxicity in LUHMES cells.

Moreover, when cells are treated with erastin, HT_pHPL and HT_pHPL-GB according to the invention protect the cells from death by ferroptosis. This result was validated with two different assays.

Together these results show that HT_pHPL and HT_pHPL-GB are very good preparations that protect dopaminergic cells from death induced by a potent neurotoxin and without inducing morphologic modification. Moreover, the heat-treated pHPL is intended to be used in biotherapy, especially through brain administration. Thus, the fact that the heat-treated pHPL is free of fibrinogen as well as proteolytic enzymes, demonstrates the potential of the heat-treated pHPL for this purpose.

Example 2: In Vivo Experiment

This in vivo experiment is performed in order to demonstrate the neuroprotective effect of heat-treated pooled human platelet lysate according to the invention. The effect is compared with the effect obtained with Riluzole drug, i.e the only known effective treatment in ALS.

All experiments were carried out in accordance with the "Principles of Laboratory Animal Care" (NIH publication 86-23, revised in 1985) and the current French and European Union legislative and regulatory framework on animal experimentation (The Council of the European Communities Directive 86/609).

The mice enrolled were FVB-Tg(Sod1*G86R)M1Jwg/J mice from JAX laboratories. Animals were group-housed (10 per cage) in a temperature-controlled room (22±2° C.) with a 12/12-hour light/dark cycle. Food and water were feed ad-libitum. After reception, the animals had a 7-day habituation period with no handling. Breeding was realized (since 2013 may) in SOPF facility and genotyping is performed by qPCR (from tail biopsy). Animal are identified with earrings.

Materials and Methods

Intermittent I.C.V Injection and Riluzole Administration

Mice were handled and weighted at the age of 60 days. Canula implantation in intra cerebro-ventricular (ICV) by stereotaxie start at this date and mice are acclimated during 1 week.

The Riluzole drug was mixed in a defined diet and formulated in pellets. Riluzole was administrated per os. (Gurney and al, Neurology, 1998). Then they were evaluated, twice a week (i.e. body weight and neuroscore), from the age of 67 days to their death.

Treatment in SOD1m-FVB and WT-FVB Males:

Two different treatments are performed from 75 days to death:

HT_pHPL prepared as described in example 1 and at 1 g/L, pH 7.4 versus vehicle. The dose of HT_pHPL administrated by intermittent ICV was 4 µL, three times a week at rate of 0.5 µL/min. Injection time: 8 min.

Riluzole drug was administrated per os at 44 mg/Kg/day.

Experimental Groups:

| | |
|---|---|
| Males WT-FVB + vehicle | Females WT-FVB + Riluzole |
| Males WT-FVB + HT_pHPL | Females SOD1m-FVB + Riluzole |
| Males WT-FVB + Riluzole | |
| Males SOD1m-FVB + vehicle | |
| Males SOD1m-FVB + HT_pHPL | |
| Males SOD1m-FVB + Riluzole | |

Results

1. Riluzole Body Weight

As shown in FIG. 4, restricted food intakes have no effect in body weight evolution in WT mice. In Tg mice, we can observe a body weight decrease at Day 88 for males and for females.

2. HT_pHPL Body Weight

As shown in FIG. 5, HT_pHPL treatment had no effect in WT males. A body weight decrease is observed at Day 88 in Tg mice treated by HT_pHPL, said treatment also induces an important delay in the pre-mortem body weight in males from Day 124.

3. Survival Curve

As shown in FIG. 6, Riluzole drug have an effect in the death initiate in Tg Males (from Day 91 to Day 102) but have no effect in survival duration.

In agreement with the delay in the pre-mortem body weight, HT_pHPL treatment delayed the onset of the death to 14 days (Day 91 at Day 105) and extended survival duration up to 48 days for Tg males (Day 123 to Day 171).

In conclusion, in vivo experiments demonstrate that the heat-treated pooled human platelet lysate according to the invention exhibit a neuroprotective effect. These results obtained in amyotrophic lateral sclerosis can be applied to other disorders wherein a loss of neurons is also observed.

REFERENCES

1. Huang E J, Reichardt L F. Neurotrophins: roles in neuronal development and function. Annu Rev Neurosci 2001; 24: 677-736.
2. Mohapel P, Frielingsdorf H, Haggblad J, et al. Platelet-derived growth factor (PDGF-BB) and brain-derived neurotrophic factor (BDNF) induce striatal neurogenesis in adult rats with 6-hydroxydopamine lesions. Neuroscience 2005; 132: 767-76.
3. Gonzalez-Aparicio R, Flores J A, Fernandez-Espejo E. Antiparkinsonian trophic action of glial cell line-derived neurotrophic factor and transforming growth factor beta 1 is enhanced after co-infusion in rats. Experimental Neurology 2010; 226: 136-47.
4. Kirik D, Georgievska B, Bjorklund A. Localized striatal delivery of GDNF as a treatment for Parkinson disease. Nat Neurosci 2004; 7: 105-10.
5. Golebiewska E M, Poole A W. Platelet secretion: From haemostasis to wound healing and beyond. Blood Rev 2014.
6. Burnouf T, Goubran H A, Chen T M, et al. Blood-derived biomaterials and, platelet growth factors in regenerative medicine. Blood Rev 2013; 27: 77-89.
7. Burnouf T, Strunk D, Koh M, et al. Human platelet lysate: replacing fetal bovine serum as a gold standard for human cell propagation? Biomaterials 2016; 76: 371-87.
8. Hayon Y, Dashevsky O, Shai E, et al. Platelet lysates stimulate angiogenesis, neurogenesis and neuroprotection after stroke. Thromb Haemost 2013; 110: 323-30.
9. J. K. Ryu, D. Davalos and K. Akassoglou. Fibrinogen signal transduction in the nervous system. Journal of thrombosis and heamostasis. 2009; Vol. 7, issue supplement s1, 151-154.
10. Tsu-Bi Shih D, Burnouf T. Preparation, quality criteria, and properties of human blood platelet lysate supplements for ex vivo stem cell expansion. New Biotechnology 2015; vol 32, number 1.
11. Victor E. Santo, Manuela E. Gomes, Joao F. Mano and Rui L; Reis. Chitosan-chondrotin sulphate nanoparticles for controlled delivery of platelet lysates in bone regenerative medicine. Journal of Tissue Engineering and Regenerative Medicine. December 2012, vol. 6, issue S3, pages s47-s59.

12. Scholz D, Poltl D, Genewsky A, et al. Rapid, complete and large-scale generation of post-mitotic neurons from the human LUHMES cell line. J Neurochem 2011; 119: 957-71.

The invention claimed is:

1. A method for treatment of a neurological disorder, comprising the step of administering a heat-treated pooled human platelet lysate to a patient or subject in need thereof, wherein the heat-treated pooled human platelet lysate has a fibrinogen content of less than 5% by weight of the fibrinogen content of non-heat-treated pHPL and a fibrinogen content of less than 50 ng/mL.

2. The method according to claim 1, wherein said heat-treated pooled human platelet lysate has a fibrinogen content of less than 3% by weight of the fibrinogen content of non-heat-treated pHPL and a fibrinogen content of less than 30 ng/mL.

3. The method according to claim 1, wherein said heat-treated pooled human platelet lysate has a fibrinogen content of less than 1% by weight of the fibrinogen content of non-heat-treated pHPL and a fibrinogen content of less than 15 ng/mL.

4. The method according to claim 1, wherein the neurological disorder is selected from neurodegenerative disorders, neuro inflammatory disorders, neurodevelopment disorders, neurovascular disorders and cerebral insults.

5. The method according to claim 4, wherein the neurological disorder is a neurodegenerative disorder selected from multiple sclerosis (MS), Parkinson's disease (PD), Huntington's disease (HD), Amyotrophic lateral sclerosis (ALS), stroke, age-related macular degeneration (AMD), Alzheimer's disease (AD), vascular dementia, frontotemporal dementia, semantic dementia and dementia with Lewy bodies.

6. The method according to claim 5, wherein the neurodegenerative disorder is selected from Parkinson's disease, amyotrophic lateral sclerosis, age-related macular degeneration and Alzheimer's disease.

7. The method according to claim 4, wherein the neurological disorder is a cerebral insult selected from hypoxia or traumatic brain injury.

8. The method according to claim 1, wherein said heat-treated pooled human platelet lysate is administrated by intrathecal, intraocular, intranasal or intra cerebroventricular route.

9. The method according to claim 8, wherein said heat-treated pooled human platelet lysate is administrated by intra cerebroventricular route.

10. The method according to claim 9, wherein said heat-treated pooled human platelet lysate is adapted to be administered with a programmable medication pump.

11. The method according to claim 8, wherein said heat-treated pooled human platelet lysate is administrated into the right lateral ventricle.

12. The method according to claim 8, wherein said heat-treated pooled human platelet lysate is administrated closed to the intraventricular foramen.

13. The method according to claim 8, wherein said heat-treated pooled human platelet lysate is administrated into the third ventricle.

* * * * *